(12) United States Patent
Adesokan et al.

(10) Patent No.: US 12,144,842 B2
(45) Date of Patent: Nov. 19, 2024

(54) PROCESS OF PREPARATION OF GLYCAN COMPOSITIONS AND USES THEREOF

(71) Applicant: Gnubiotics Sciences SA, Epalinges (CH)

(72) Inventors: Adeyemi Adesokan, Lausanne (CH); Jean-Philippe Kunz, Verbier (CH)

(73) Assignee: Gnubiotics Sciences SA, Epalinges (CH)

( * ) Notice: Subject to any disclaimer, the term of this patent is extended or adjusted under 35 U.S.C. 154(b) by 228 days.

(21) Appl. No.: 16/975,384

(22) PCT Filed: Feb. 22, 2019

(86) PCT No.: PCT/EP2019/054413
§ 371 (c)(1),
(2) Date: Aug. 24, 2020

(87) PCT Pub. No.: WO2019/162425
PCT Pub. Date: Aug. 29, 2019

(65) Prior Publication Data
US 2020/0397861 A1    Dec. 24, 2020

(30) Foreign Application Priority Data

Feb. 22, 2018  (EP) .................................. 18158116
Jul. 11, 2018  (EP) .................................. 18182825

(51) Int. Cl.
| | | |
|---|---|---|
| *A61K 38/17* | (2006.01) | |
| *A23K 20/147* | (2016.01) | |
| *A23K 20/163* | (2016.01) | |
| *A23L 33/00* | (2016.01) | |
| *A23L 33/125* | (2016.01) | |
| *A23L 33/18* | (2016.01) | |
| *A61K 31/715* | (2006.01) | |

(52) U.S. Cl.
CPC ........ *A61K 38/1735* (2013.01); *A23K 20/147* (2016.05); *A23K 20/163* (2016.05); *A23L 33/125* (2016.08); *A23L 33/18* (2016.08); *A23L 33/40* (2016.08); *A61K 31/715* (2013.01); *A23V 2002/00* (2013.01)

(58) Field of Classification Search
CPC .............. A61K 38/1735; A61K 31/715; A23K 20/147; A23K 20/163; A23L 33/125; A23L 33/18; A23L 33/40; A23V 2002/00
See application file for complete search history.

(56) References Cited

U.S. PATENT DOCUMENTS

| | | |
|---|---|---|
| 5,064,674 A | 11/1991 | Girsh |
| 5,141,925 A | 8/1992 | Alroy |
| 8,795,746 B2 | 8/2014 | Sonnenburg |
| 2011/0085981 A1 | 4/2011 | Wang |
| 2017/0151268 A1 | 6/2017 | Von Maltzahn |
| 2017/0299530 A1 | 10/2017 | Yang |
| 2017/0322219 A1 | 11/2017 | Wandall et al. |

FOREIGN PATENT DOCUMENTS

| | | | |
|---|---|---|---|
| CA | 2646021 A1 * | 10/2007 | ......... A01K 67/0276 |
| WO | WO 2007/114307 A1 | 10/2007 | |
| WO | WO 2008/147405 A1 | 12/2008 | |
| WO | WO-2016/122889 A1 | 8/2016 | |
| WO | WO 2019/049157 A1 | 3/2019 | |

OTHER PUBLICATIONS

Schömig, Veronika J., et al. "An optimized purification process for porcine gastric mucin with preservation of its native functional properties." *RSC advances* 6.50 (2016): 44932-44943.
Roberton, A. M., et al. "The putative 'link' glycopeptide associated with mucus glycoproteins. Composition and properties of preparations from the gastrointestinal tracts of several mammals." *Biochemical Journal* 261.2 (1989): 637-647.
Dekker, J., P. H. Aelmans, and G. J. Strous. "The oligomeric structure of rat and human gastric mucins." *Biochemical Journal* 277.2 (1991): 423-427.
Derrien, Muriel, et al. "Mucin-bacterial interactions in the human oral cavity and digestive tract." *Gut microbes* 1.4 (2010): 254-268.
Robbe, Catherine, et al. "Structural diversity and specific distribution of O-glycans in normal human mucins along the intestinal tract." *Biochemical Journal* 384.2 (2004): 307-316.
Gopal, Pramod K., and H. S. Gill. "Oligosaccharides and glycoconjugates in bovine milk and colostrum." *British Journal of Nutrition* 84.S1 (2000): 69-74.
Koropatkin et al., "How glycan metabolism shapes the human gut microbiota." 2012, Nat Rev Microbiol. 10(5):323-335.
Derrien, Muriel, et al. "*Akkermansia muciniphila* gen. nov., sp. nov., a human intestinal mucin-degrading bacterium." *International journal of systematic and evolutionary microbiology* 54.5 (2004): 1469-1476.
Chia, Loo Wee, et al. "Deciphering the trophic interaction between Akkermansia muciniphila and the butyrogenic gut commensal Anaerostipes caccae using a metatranscriptomic approach." *Antonie Van Leeuwenhoek* 111.6 (2018): 859-873.
Tailford, Louise E., et al. "Mucin glycan foraging in the human gut microbiome." *Frontiers in genetics* 6 (2015): 81.
Ahmed, Ishfaq, et al. "Altered mucus composition and bacterial dysbiosis promote development of colitis following chronic Notch inhibition." (2016): 3297-3297.
Song, Xuezheng, et al. "Oxidative release of natural glycans for functional glycomics." *Nature methods* 13.6 (2016): 528-534.
Kumar, Pavan, et al. "Perspective of membrane technology in dairy industry: A review." *Asian-Australasian Journal of Animal Sciences* 26.9 (2013): 1347.

(Continued)

*Primary Examiner* — Jeanette M Lieb
*Assistant Examiner* — Erinne R Dabkowski
(74) *Attorney, Agent, or Firm* — Foley & Lardner LLP

(57) ABSTRACT

The present invention relates to a glycan composition useful as nutritional supplement, such as for instant formula supplement and as nutraceutical products and a method of preparation thereof.

19 Claims, 6 Drawing Sheets

(56) References Cited

OTHER PUBLICATIONS

Jeromin, Alice. "Food allergy: Fact versus fiction Takeaways to help veterinarians deal with food allergies in pets." https://www.veterinarypractice news.com/food-allergy-november-2018-2/.
Elliott, Chester H. "The antigenic properties of glycoproteins." *The Journal of Infectious Diseases* (1914): 501-517.
Green, Terry "Specializing in Recycling with Black Soldier Fly Technologies." https://www.dipterra.com/blog/bsfl-an-earth-friendly-feedstock. Jan. 13, 2013.
Celli, Jonathan, et al. "Viscoelastic properties and dynamics of porcine gastric mucin." *Biomacromolecules* 6.3 (2005): 1329-1333.
Corfield, Anthony P., et al. "Mucins in the gastrointestinal tract in health and disease." *Front Biosci* 6.10 (2001): 1321-1327.
Haffner, et al., "Amino Acids in Animal Nutrition." AgriMedia. ISBN 3-86037-126-6. © 2000 Agrimedia GmbH. Year: 2000.
Brochure "Mucopro 80P: Pure Guts Power," Darling Ingredients, 4 pages.
International Search Report in International Application No. PCT/EP2019/081852, issued Apr. 7, 2020.
International Search Report in International Application No. PCT/EP2019/054413, issued Apr. 26, 2019.
Non-final Office Action issued in U.S. Appl. No. 16/687,665, dated Oct. 30, 2020.
Final Office Action issued in U.S. Appl. No. 16/687,665, dated Apr. 9, 2021.
Non-final Office Action issued in U.S. Appl. No. 16/687,665, dated Dec. 14, 2021.
Final Office Action issued in U.S. Appl. No. 16/687,665, dated Mar. 15, 2022.
Communication Pursuant to Article 94(3) EPC, EP 19705369.7, dated Oct. 25, 2022, 3 pages.
Foreign Action other than Search Report on EP 19705369.7 DTD Oct. 25, 2022.

\* cited by examiner

PROCESS OF PREPARATION OF GLYCAN COMPOSITIONS AND USES THEREOF

RELATED APPLICATIONS

This application is a national stage filing under 35 U.S.C. 371 of International Application No. PCT/EP2019/054413, filed Feb. 22, 2019, which claims priority to European Application No. 18158116.6, filed Feb. 22, 2018 and European Application No. 18182825.2, filed Jul. 11, 2018. The entire teachings of the above applications are incorporated herein by reference. International Application No. PCT/EP2019/054413 was published under PCT Article 21 (2) in English.

FIELD OF THE INVENTION

The present invention pertains generally to the fields of glycan compositions and products derived therefrom, in particular glycan compositions useful as nutritional supplements, such as infant formula supplement, medical nutrition, domestic animal nutrition, adjuvant for on-going treatments, cancer therapeutics and nutraceuticals products that enhance the growth of beneficial microorganisms in the mammalian microbiome, such as *Akkermansia muciniphila*.

BACKGROUND OF THE INVENTION

It has been recognized that the dense microbial community (microbiota) present in the mammalian, and in particular human, intestine shortly after birth and throughout the life has a profound effect on health and physiology.

One major factor shaping the composition and physiology of the microbiota is the influx of glycans into the intestine, mostly from diet and host mucosal secretions. Humans consume dozens of different plant and animal-derived dietary glycans, most of which cannot be degraded by enzymes encoded in the human genome. Microbial fermentation transforms these indigestible glycans into short chain fatty acids which serve as nutrients for colonocytes and other gut epithelial cells. Gut microorganisms therefore play a pivotal symbiotic role in helping mammals (e.g., humans) access calories from otherwise indigestible nutrients and each type of microorganisms prefer different glycans. Therefore, a selective consumption of nutrients can influence which microbial groups proliferate and persist in the gastrointestinal tract. Dietary glycans have been considered as being a possible non-invasive strategy of directly influencing the balance of bacterial species in the gut (Koropathkin et al., 2012, *Nat Rev Microbiol.* 10(5):323-35).

Gut microbes play an important role in the regulation of host metabolism and low-grade inflammation. Abnormalities in microbiota composition and activity (called dysbiosis) have been implicated in the emergence of the metabolic syndrome, which include diseases such as obesity, type 2 diabetes and cardiovascular diseases. One of the bacteria that influence human metabolism and is found in infant and adult intestinal track (0.5-5% of the total bacteria) as well as in human milk is *Akkermansia muciniphila* (Derrien et al., 2008, *Appl Environ Microbiol.*, 74(5): 1646-1648; Cani et al., 2017, *Front Microbiol.*, 8: 1765).

*Akkermansia muciniphila* is a Gram-negative, anaerobic, non-spore-forming bacterium, within genus *Akkermansia*, from the family—Verrucomicrobiaceae, which is the most abundant mucus degrading bacterium in the healthy individual. The host and *Akkermansia* communicate continually and this interaction creates a positive feedback loop in which *Akkermansia* degrades the mucus layer which stimulates new mucus production and the production of new mucus stimulates growth of *Akkermansia*. This process ensures that abundant amounts of *Akkermansia* maintain the integrity and shape of the mucus layer. *Akkermansia* produces important metabolites as a result of the mucus degradation process, in particular two very important short chain fatty acids (SCFA): acetic acid and propionic acid, which trigger a cascade of responses in the host having a crucial role in immune stimulation and metabolic signaling (Derrien et al., 2011, *Front Microbiol.*, 2: 166).

Recent evidence demonstrates that gut concentration of *A. muciniphila* is inversely associated with obesity, diabetes, cardiometabolic diseases and low-grade inflammation. Therefore, this bacterium is considered a potential candidate for improving the conditions of subjects suffering or at risk of suffering from those disorders (Cani et al., 2017, supra).

In particular, *A. muciniphila*'s numbers were higher in pregnant women with normal weight gain than in those with excessive weight gain (Santacruz et al., 2010, *Br J Nutr.*, 104(1):83-92) and *Akkermansia muciniphila*-like bacteria were significantly lower in the obese/overweight pre-school children (Karlsson et al., 2012, *Obesity*, 20(11): 2257-61). *A. muciniphila* was also shown to inversely correlate with the onset of inflammation, altered adipose tissue metabolism and metabolic disorders during obesity in mice (Schneeberger et al., 2015, *Scientific Reports*, 5: 16643) and was shown to improve metabolic health during a dietary intervention (calorie restriction) in overweight/obese adults (Dao et al., 2016, *Gut*, 65(3): 426-36). *A. muciniphila* was also shown to be inversely related to the severity of the acute appendicitis (Swidsinski et al., 2011, *Gut*, 60(1):34-40) and was suggested to play a protective role in autoimmune diabetes development, particularly during infancy (Hansen et al., 2012, *Diabetologia*, 55(8):2285-94). Further, and not least, a correlation between clinical responses to immune checkpoint inhibitors (ICIs) targeting the PD-1/PD-L1 axis (Programmed cell death protein 1/Programmed death-ligand 1) in cancer patients (non-small cell lung carcinoma, renal cell carcinoma) and the relative abundance of *A. muciniphila* was found. In particular, it was shown that fecal microbiota transplantation (FMT) from cancer patients who responded to ICIs into germ-free or antibiotic-treated mice ameliorated the antitumor effects of PD-1 blockade (Routy et al., 2017, *Science*, 359(6371):91-97).

A possibility that has been investigated to enhance the population of *A. muciniphila* in the gut is the administration of live or pasteurized *A. muciniphila* in the form of oral supplementation. There is an issue, however, of preserving the viability of *A. muciniphila* during production and storage prior to administration of those supplements Cani et al., 2017, supra). No commercially available probiotic supplement currently exists that contains *Akkermansia muciniphila*. Alternatively, increasing *Akkermansia muciniphila* can be achieved through the consumption of certain prebiotics and polyphenol-rich foods. However, the efficacy of those prebiotics and polyphenol-rich foods is limited.

In addition, cell surface glycans and glycopeptides have been implicated in protecting cancer cells against the immune system and therefore targeting these glycans and glycopeptides with exogenously administered or endogenously induced antibodies may represent a therapeutic strategy (Rodriguez et al., 2018, *Nat Rev Immunol.*, February 5. doi: 10.1038/nri.2018.3). Exposure to these glycans prior to or in the early stages of cancer may induce such endogenous antibodies and/or prime the immune system for treatment with the exogenously administered antibodies.

Therefore, there is a need to develop glycan compositions which would be accessible to *Akkermansia muciniphila* and provide for an increase in this bacterium population in the human intestinal track. Such a need is present in both healthy humans and humans with disorders such as obesity, diabetes and immune dysfunctions or undergoing a cancer immunotherapy. In addition there is a need to develop glycan compositions which would stimulate the immune system to recognize cancer cell-borne cell surface glycans and attack such cancer cells.

SUMMARY OF THE INVENTION

An object of this invention is to provide a new glycan composition which is able to promote and/or to stimulate *Akkermansia muciniphila* growth, in particular a new glycan composition which is able to reverse a dysbiosis in a mammal (e.g., a human) by promoting the growth of beneficial gut bacteria, e.g., *Akkermansia muciniphila*.

Another object of this invention is to provide a method for the preparation of a glycan composition which is promoting *Akkermansia muciniphila* growth, in particular a new glycan composition which is able to reverse a dysbiosis in a mammal (e.g., a human) by promoting the growth of beneficial gut bacteria, e.g., *Akkermansia muciniphila*.

It is advantageous to provide a method for the preparation of a glycan composition having a higher concentration in glycopeptides compared to free glycans. Without being bound by theory the present inventors believe that the glycans present on glycopeptides may be better utilized than free glycans by certain beneficial bacteria in the microbiota, such as *Akkermansia muciniphila*.

It is advantageous to provide a method for the preparation of a glycan composition having low glucose concentration. Without being bound by theory the present inventors believe that higher glucose concentration tend to inhibit the growth of certain beneficial bacteria in the microbiota, such as *Akkermansia muciniphila*.

It is advantageous to provide a method for the preparation of a glycan composition that allows large scale manufacturing.

Objects of this invention have been achieved by providing a method according to claim 1, a composition according to claim 7 or 8 and a nutritional or food supplement according to claim 12.

Disclosed herein, according to a first aspect of the invention, is a method for the preparation of a mixture of glycans and glycopeptides comprising the steps of:
  (a) providing an isolated source of gastrointestinal tract mucins;
  (b) releasing and reducing glycans and producing glycopeptides from the isolated source of gastrointestinal tract mucins in aqueous medium by dissolving the gastrointestinal tract mucins in 0.1 M to 0.6 M NaOH resulting in a solution having a pH of less than about 11.5, and treating the dissolved gastrointestinal tract mucins with a reducing agent selected from 0.5 M to 1M NaBH$_4$, LiBH$_4$, LiAlH$_4$ or Na(BH$_3$CN) or 1-2M Diisobutyl Aluminum hydride (DIBAL-H);
  (c) neutralizing the resulting solution from step (b) to a pH of between 6.8 and 7.2 by addition of an acid;
  (d) contacting the neutralized solution with diatomaceous earth and separating the diatomaceous earth from any liquid phase;
  (e) further filtering the liquid phase obtained under step (d) through a 1-3 kDa cutoff filter;
  (f) collecting the filtrate as a mixture of glycans and glycopeptides.

According to a further aspect, is provided a mixture of glycans and glycopeptides, obtainable from a process according to the invention.

According to a further aspect, is provided a mixture of glycans and glycopeptides obtained from a gastrointestinal tract mucins and having a glycopeptide: free glycan ratio of equal to or greater than 1:1.

According to another particular aspect of the invention, is provided a mixture of glycans and glycopeptides obtained from gastrointestinal tract mucins and comprising more than 25, but less than 100, in particular less than 50 different free glycans.

According to a further aspect, is provided a nutritional or dietary composition or nutritional or dietary premix according to the invention, wherein said composition or premix is an infant formulation.

According to a further aspect, is provided a nutritional or dietary composition or nutritional or dietary premix according to the invention for ingestion by a non-infant human, e.g., a pre-adolescent human, a teenaged human, an adult human, or an aged adult human.

According to another further aspect, is provided a nutritional or dietary composition or nutritional or dietary premix according to the invention, wherein said composition or premix is foodstuff for a domestic animal.

According to another aspect, is provided a pharmaceutical composition comprising at least one a mixture of glycans and glycopeptides according to the invention and a pharmaceutically acceptable carrier, diluent or excipient thereof.

According to another aspect, is provided mixture of glycans and glycopeptides according to the invention for use in the prevention and/or treatment of an unbalance of the microbiota and/or disorders associated with dysbiosis such as asymptomatic dysbiotic microbiota, in particular gut microbiota having depleted *Akkermansia muciniphila*.

According to another further aspect of the invention, is provided a mixture of glycans and glycopeptides according to the invention for use in the treatment of a metabolic disorder such as obesity or metabolic syndrome, diabetes, in particular autoimmune diabetes.

According to another further aspect of the invention, is provided a mixture of glycans and glycopeptides according to the invention for use in the treatment of a cancer, in particular in combination with immunotherapy, radio therapy or chemotherapy.

According to another aspect, is provided a use of a mixture of glycans and glycopeptides according to the invention for the preparation of a composition useful for the prevention and/or treatment of an unbalance of the microbiota and/or disorders associated with dysbiosis such as asymptomatic dysbiotic microbiota, in particular gut microbiota having depleted *Akkermansia muciniphila*.

According to another further aspect of the invention, is provided a method of preventing and/or treating an unbalance of the microbiota and/or disorders associated with dysbiosis such as asymptomatic dysbiotic microbiota, in particular gut microbiota having depleted *Akkermansia muciniphila*, in a subject in need thereof, said method comprising administering at least one a mixture of glycans and glycopeptides according to the invention in said subject.

According to another further aspect of the invention, is provided a method of increasing the prevalence of *Akkermansia muciniphila* in a mammalian subject's gut, said method comprising administering at least one a mixture of glycans and glycopeptides according to the invention in said subject.

DETAILED DESCRIPTION

Figures 1A, 1B:
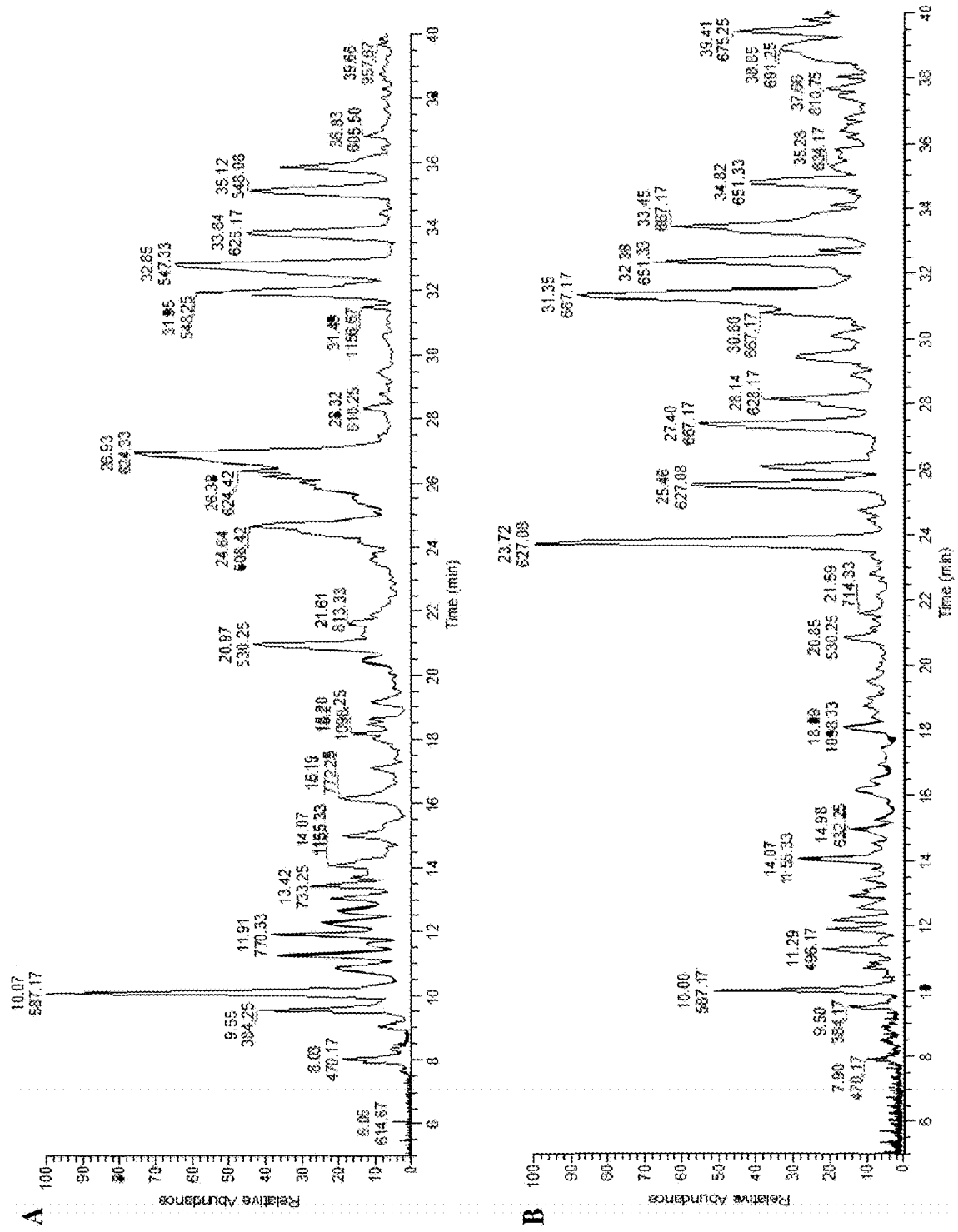
FIG. 1 shows chromatographs of compositions of the invention of Example 1 after precipitation with 80% acetone, from retention time 5-40 min, obtained by LC-MS/MS as described in Example 2 before (A-B, E) and after (C-D) passing through a C18 cartridge. A, C: C1; B, D: C2; E: comparative composition CC2. The values on top of each peak indicate the retention time (min) and m/z value, respectively.

The expression "a source of gastrointestinal tract mucins" encompasses any natural source of mucin from which glycans and glycopeptides can be extracted, suitable for mammalian nutrition or pharmaceutical use. Typical sources of gastrointestinal tract mucins are extracts from gastrointestinal tract, in particular from porcine source or from bovine source.

The expression "Infant" refers to a child under the age of 12 months.

The expression "Infant formula" refers to foodstuff intended for the complete nutrition of infants during the first 6-12 months of life.

The expression "pre-adolescent human" refers to a human of between 1 and 12 years of age.

The expression "teenaged human" refers to a human of between 13 and 18 years of age.

The expression "adult human" refers to a human of over 18 years of age.

The expression "aged adult human" refers to a human over 55 years of age.

The expression "subject" refers to mammals. For examples, mammals contemplated by the present invention include human, primates, domesticated animals such as cattle, sheep, pigs, horses, rodents, cats, dogs and other pets.

The expression "domestic animal" refers to cattle, sheep, pigs, horses, other farm mammals, rodents, cats, dogs and other pets.

The expression "nutritional supplement" means any comestible material having a nutritional value suitable for mammalian nutrition which can be used either alone as such or in combination with standard foodstuff.

The expression "complete food" means nutritionally complete and balanced food compositions.

The expression "feed additives" means products used in animal nutrition for purposes of improving the quality of feed and the quality of food from animal origin, or to improve the animals' performance and health, e.g. providing enhanced digestibility of the feed materials.

The expression "animal food" and in particular "pet food" means foodstuff suitable for animal nutrition. Substances such as nutrients and ingredients, in particular all the recommended vitamins and minerals suitable for nutritionally complete and balanced animal feed compositions, and recommenced amounts thereof, may be found for example, in the Official Publication of The Association of American Feed Control Officials, Inc. (AAFCO), Atlanta, GA, 2017 or in National Research Council, 2006, Nutritional Guidelines from the European Pet Food Industry Federation or Association of American Feed Control Officials, Official Publication, 2015.

According to a particular embodiment, "dry" means that the water content is less than 5 weight-% (wt-%), based on the total weight of the composition, premix or formulation.

The term "diatomaceous earth" that is also known as D.E., diatomite, or kieselgur/kieselguhr, means a naturally occurring, soft, siliceous sedimentary rock that is easily crumbled into a fine white to off-white powder. It has a particle size ranging from less than 3 μm to more than 1 mm, but typically 10 μm to 200 μm. Depending on the granularity, this powder can have an abrasive feel, similar to pumice powder, and has a low density as a result of its high porosity. The typical chemical composition of oven-dried diatomaceous earth is 80 to 90% silica, with 2 to 4% alumina (attributed mostly to clay minerals) and 0.5 to 2% iron oxide.

The expression "different free glycans", such as in the expression "more than 25 but less than 100 different free glycans" means glycans that have been released from protein or peptide and that have a chemical structure unique from other glycan chemical structures in the mixture.

The term excludes both glycans that are still bound to protein or peptide and peeling products of glycans.

The term "protein" or "glycopeptides" refers to peptides linked to oligosaccharides, e.g. peptides either N-linked or O-linked to oligosaccharides.

METHODS ACCORDING TO THE INVENTION

According to a particular aspect of the invention, it has been unexpectedly found that by using a method according to the invention, a new mixture of glycans and glycopeptides can be prepared that presents the unexpected ability to better stimulate the growth of *Akkermansia muciniphila* as compared to prior art glycan preparations.

According to a particular aspect of the invention, it has been found that by using a metal hydride as a reducing agent in a method of the invention at the concentrations described herein, it was possible to advantageously prepare a mixture of glycans and glycopeptides wherein the ratio of glycopeptides:free glycans (w/w) (carbohydrate) is equal to or greater than 1:1, in particular from about a 1:1 to about a 2:1 ratio of glycopeptide:free glycans (w/w) which mixtures can be advantageously used according to the invention.

According to a particular aspect of the invention, is provided a method for the preparation of a mixture of glycans and glycopeptides comprising the steps of:
(a) providing an isolated source of the gastrointestinal tract mucins;
(b) releasing and reducing glycans and glycopeptides from the gastrointestinal tract mucins in aqueous medium by dissolving the gastrointestinal tract mucins in 0.1 M to 0.6 M NaOH at room temperature under stirring resulting in a solution having a pH of less than about 11.5 (e.g., less than about 11.4, less than about 11.3, less than about 11.2, less than about 11.1, less than about 11.0) and treating the dissolved gastrointestinal tract mucins with a reducing agent selected from 0.5 M to 1 M NaBH$_4$, LiBH$_4$, LiAlH$_4$ or Na(BH$_3$CN) or 1 to 2M Diisobutyl Aluminum hydride (DIBAL-H), at a temperature between about 5-10° C.;

(c) neutralizing the resulting solution from step (b) to a pH of between 6.8 and 7.2 by addition of an acid;

(d) contacting the neutralized solution with diatomaceous earth and separating the diatomaceous earth from any liquid phase;

(e) further filtering the liquid phase obtained under step (d) through a 1-3 kDa cutoff filter;

(f) collecting the filtrate as a mixture of glycans and glycopeptides.

According to another particular aspect of the invention, is provided a method for the preparation of a mixture of glycans and glycopeptides according to the invention as described herein, wherein step (b) comprises the steps of:

b1. dissolving the gastrointestinal tract mucins in 0.1 M to 0.6 M NaOH resulting in a solution having a pH of less than about 11.5;

b2. treating the dissolved gastrointestinal tract mucins with the said reducing agent at a temperature between about 5-10° C. under vigorous stirring for about 5 to 8 minutes;

b3. maintaining stiffing for about 40 to 60 minutes while bringing the obtained mixture to room temperature;

b4. Heating the reaction mixture to a temperature to about 35 to 50° C. and maintaining the reaction mixture at this temperature under stiffing for about 8 to 25 hours.

It was found that maintaining the pH below about 11.5 during step b1 results in less ß-elimination and therefore less release of glycans from the glycoproteins in the mucin, while still allowing for hydrolysis of the glycoproteins. Because mucins are slightly acidic, the dissolution of a high enough concentration of mucin in NaOH in step b1 (e.g., greater than about 2 g mucin/100 ml solution) lowers the pH of the solution from an initial pH of 11.5-12.5 to a pH of below about 11.5 (typically from 10.5 to less than 11.5). This results in a higher glycopeptide:free glycan ratio than prior art preparations, which either use a base to maintain the pH of the mucin solution above 11.5, or use lower concentrations of mucin that do not lower the pH to below 11.5 when it is solubilized. It will be readily apparent to one of skilled in the art, that when lower concentrations of mucin are used in processes of the present invention, obtaining a pH of below about 11.5 may require either lower concentrations of NaOH (or another base) or the use of an appropriate acid added to the solubilized mucin prior to the addition of the reducing agent.

Exemplary reducing agents, amounts thereof and conditions to produce a composition having a glycopeptide:free glycan (carbohydrate) ratio of equal to or greater than 1:1 are set forth in Table 1 below:

In particular, is provided a method for the preparation of a mixture of glycans and glycopeptides comprising the steps of:

(a) providing an isolated source of the gastrointestinal tract mucins;

(b) releasing and reducing glycans and glycopeptides from the gastrointestinal tract mucins in aqueous medium by dissolving the gastrointestinal tract mucins in 0.1 M to 0.6 M NaOH at room temperature under stiffing resulting in a solution having a pH of less than about 11.5 and treating the dissolved gastrointestinal tract mucins with 0.5 M to 1 M, preferably 0.8 to 1M NaBH$_4$ at a temperature between about 5-10° C.;

(c) neutralizing the resulting solution from step (b) to a pH of between 6.8 and 7.2 by addition of an acid;

(d) contacting the neutralized solution with diatomaceous earth and separating the diatomaceous earth from any liquid phase;

(e) further filtering the liquid phase obtained under step (d) through a 1-3 kDa cutoff filter;

(f) collecting the filtrate as a mixture of glycans and glycopeptides.

According to another particular aspect of the invention, is provided a method for the preparation of a mixture of glycans and glycopeptides according to the invention, wherein step (b) comprises the steps of:

b1. dissolving the gastrointestinal tract mucins in 0.1 M to 0.6 M NaOH resulting in a solution having a pH of less than about 11.5 (e.g., less than about 11.4, less than about 11.3, less than about 11.2, less than about 11.1, less than about 11.0);

b2. treating the dissolved gastrointestinal tract mucins with 0.8 M to 1 M NaBH$_4$ at a temperature between about 5-10° C. under vigorous stirring for about 5 to 8 minutes; b3. maintaining stiffing for about 40 to 60 minutes while bringing the obtained mixture to room temperature;

b4. Heating the reaction mixture to a temperature to about 45 to 50° C. and maintaining the reaction mixture at this temperature under stirring for about 15 to 24 hours.

According to another particular aspect of the invention, is provided a method for the preparation of a mixture of glycans and glycopeptides according to the invention, wherein in step (b) of dissolving the gastrointestinal tract mucins is carried in 0.1 M to 0.6 M NaOH, in particular in 0.2 M to 0.6 M NaOH.

According to another particular aspect of the invention, the pH throughout step (b) is between 10.5 and less than 11.5, for example less than about 11.4, less than about 11.3, less than about 11.2, less than about 11.1, less than about 11.0 by the addition of acid, if necessary.

According to another particular aspect of the invention, is provided a method for the preparation of a mixture of glycans and glycopeptides according to the invention, wherein in step (b) the dissolved gastrointestinal tract

TABLE 1A

| Reducing agent | NaBH$_4$ | LiBH$_4$ | Na(BH$_3$CN) | LiAlH$_4$ | DIBAL-H |
|---|---|---|---|---|---|
| Concentration used at step b2 | 0.5-1 M | 0.5-1 M | 0.5-1 M | 0.5-1 M | 1-2 M |
| Temperature during step b4 | 40-48° C. | 40-48° C. | 40-48° C. | 35-40° C. | 40-45° C. |
| Duration of step b4 | 15-20 h | 15-20 h | 20-25 h | 8-10 h | 12-15 h |
| pH of solubilized mucin prior to addition of reducing agent | 10.5.-11.5 | 10.5-11.5 | 10.5-11.5 | 10.5-11.5 | 10.5-11.5 | mucins are treated with 0.8 M to 1 M NaBH$_4$, more preferably in 0.9 M to 1 M NaBH$_4$, and even more preferably in 1 M NaBH$_4$.

According to another particular aspect of the invention, is provided a method for the preparation of a mixture of glycans and glycopeptides according to the invention, wherein the neutralizing step (c) is carried out after the solution's temperature is cooled to between about 5-10° C.

According to further particular aspect of the invention, is provided a method for the preparation of a mixture of glycans and glycopeptides according to the invention, wherein the neutralizing step (c) is carried by addition of an acid selected from hydrochloric acid, sulfuric acid and phosphoric acid, in particular hydrochloric acid.

According to another particular aspect of the invention, is provided a method for the preparation of a mixture of glycans and glycopeptides according to the invention, wherein step (d) is carried out by mixing the neutralized solution from step (c) with the diatomaceous earth, followed by a filtration of the mixture through a paper filter having pore size of about 4-7 μm.

In a more specific particular aspect, the filtration through a paper filter having pore size of about 4-7 μm is carried out under pressure of about 400 to 800 mbars, for example for about 15 to about 45 minutes.

In another more specific particular aspect, the diatomaceous earth retentate from the filtration through a paper filter having pore size of about 4-7 μm is resuspended and re-filtered through the 4-7 μm paper filter one or more times and all filtrates are combined prior to step (e).

According to a further particular aspect of the invention, is provided a method for the preparation of a mixture of glycans and glycopeptides according to the invention, wherein step (e) is conducted under pressure of about 1.5 to about 2.5 bars.

According to a further particular aspect of the invention, is provided a method for the preparation of a mixture of glycans and glycopeptides according to the invention, wherein step (e) is conducted while stirring the unfiltered material.

According to another particular aspect of the invention, is provided a method for the preparation of a mixture of glycans and glycopeptides according to the invention, wherein the steps (d) and (e) are carried out at room temperature.

The product from step (f) is a liquid may contain a concentration of boron (from the NaBH$_4$ treatment) which would not be acceptable for some particular uses. In some embodiments, it is desirable to obtain a dry product with lower boron concentration. Thus, according to another particular aspect of the invention, is provided a method for the preparation of a mixture of glycans and glycopeptides according to the invention, wherein the filtrate collected under step (f) is further subjected to a concentration step (g), for example by evaporation (e.g. at a temperature from about 45 to 55° C., under vacuum).

According to another particular aspect of the invention, is provided a method for the preparation of a mixture of glycans and glycopeptides according to the invention, wherein the concentrate obtained under the concentration step (g) is subjected to a drying step (h) to collect a composition of the invention as dried product (e.g. by successive solvent evaporation). In a more specific aspect, the drying is achieved by one or more extractions with ethanol and subsequent evaporation.

Glycan Compositions According to the Invention

According to one particular aspect, a mixture of glycans and glycopeptides according to the invention is a mixture of glycans and glycopeptides (protein) obtained from gastrointestinal tract mucins comprising a glycopeptide: free glycan (carbohydrate) ratio of equal to or greater than 1:1, in particular from about a 1:1 to about a 2:1 ratio of glycopeptide:free glycan (w/w). According to another particular aspect, a mixture of glycans and glycopeptides according to the invention is a mixture of glycans and glycopeptides obtained from gastrointestinal tract mucins and comprising more than 25, but less than 100, in particular less than 50 different free glycans.

According to another particular aspect, a mixture of glycans and glycopeptides according to the invention is a mixture of glycans and glycopeptides obtained from gastrointestinal tract mucins and comprising between 70-90% (w/w) glycopeptide.

According to another aspect, is provided a mixture of glycans and glycopeptides obtained from a gastrointestinal tract mucins, comprising more than 25 different free glycans (e.g., more than 25 but less than 100 different free glycans, e.g., more than 25 but less than 50 different free glycans) and comprising a 1:1 (w/w) or greater ratio of glycopeptide:free glycan, in particular from about a 1:1 to about a 2:1 ratio of glycopeptide:free glycan (w/w). The relative carbohydrate content of a mixture can be calculated based on the glycan amounts measured by LC-MS/MS (liquid chromatography tandem-mass spectrometry) and calculated according to formula (i):

$$\text{Carbohydrate amount } (\%) = \frac{\sum (\text{glycan } m/z \times \text{charge} \times \text{ion intensity})}{\sum (m/z \times \text{charge} \times \text{ion intensity})} \quad (i)$$

wherein the 'm/z value (equivalent to molecular weight) and ion intensity (equivalent to molar concentration) of each species present in the LC-MS/MS spectra. Alternatively, the carbohydrate content may be calculated using the Orcinol-sulfuric acid method well known in the art. Other methods known in the art for determining carbohydrate content may also be used.

The relative protein content of a mixture can be determined by methods well-known in the art. Alternatively, the relative protein content of a mixture can be estimated by assuming that carbohydrate and protein make up 85-90% of a mixture of the present invention (the remaining being salt, water and ash). Thus, once one determines the carbohydrate content, the protein content can be accurately estimated by subtracting the carbohydrate content from 85% or 90%. For example, a mixture of the invention having 35% carbohydrate content would be estimated to have between 50 and 55% protein content. The term "carbohydrate content" includes carbohydrates bound to glycopeptide in the mixtures, as well as free glycans and peeling products.

According to another particular aspect of the invention, is provided a mixture of glycans and glycopeptides obtained from a gastrointestinal tract mucins, comprising more than 25 different free glycans (e.g., more than 25 but less than 100 different free glycans, e.g., more than 25 but less than 50 different free glycans). The amount of monosaccharides, such as glucose, in a composition of this invention can be measured by standard methods such as high-performance liquid chromatography (HPLC).

According to another particular aspect of the invention, the mixture of glycans and glycopeptides comprises more than 25 but less than 100 different free glycans and a 1:1 (w/w) or greater ratio of glycopeptide:free glycan.

According to another particular aspect of the invention, the mixture of glycans and glycopeptides comprises more than 25 but less than 50 different free glycans and between a 1:1 and 2:1 (w/w) ratio of glycopeptide:free glycan.

According to a further particular aspect of the invention, is provided a mixture of glycans and glycopeptides obtained from gastrointestinal tract mucin comprising at least each of the following glycan species either as free glycans or as part of a glycopeptide:

Fucα1-2Galβ1-3GalNAc;
GlcNAcα1-4Galβ1-3GalNAc;
GlcNAcα1-4Galβ1-3(GlcNAcα1-4Galβ1-4GlcNAcβ1-6)GalNAc;
Fucα1-2Galβ1-3 (6S-GlcNAcβ1-6)GalNAc;
Fucα1-2(GalNAcα1-3)Galβ1-3GalNAc;
GlcNAcα1-4Galβ1-3(Fucα1-2Galβ1-4GlcNAcβ1-6) GalNAc; and
Fucα1-2Galβ1-3(Fucα1-2Galβ1-4GlcNAcβ1-6)GalNAc.

According to another particular aspect of the invention, is provided a mixture of glycans and glycopeptides obtained from a gastrointestinal tract mucins and comprising 200 parts per million (ppm) of boron (B) or less.

According to another particular aspect, the glycans and glycopeptides mixtures of the invention can be used for the preparation of nutritional/dietary supplement or complete food, in particular for oral delivery.

According to another aspect, compositions of the invention are in the form of nutritional supplement or complete food and contain any of the above-described mixtures of glycans and glycopeptides according to the invention.

In some embodiments, the compositions are useful as an infant formula supplement. In some embodiments, compositions are useful as a human nutritional supplement.

In some embodiments, the compositions are useful as a domestic animal nutritional supplement.

The complete food or dietary/nutritional supplement according to the invention can be artificially enriched in vitamins, soluble or insoluble mineral salts or mixtures thereof or enzymes.

According to one aspect, pharmaceutical compositions of the invention contain any of the above-described mixtures of glycans and glycopeptides according to the invention and a pharmaceutically acceptable carrier, diluent or excipient thereof.

The compositions of the invention can be formulated as solid dosage forms containing a nutritional/dietary supplement with or without suitable excipients or diluents and prepared either by compression or molding methods well known in the art, encompassing compressed tablets and (molded tablets or tablet triturates. In addition to the active or therapeutic/nutritional/cosmetic ingredient or ingredients, tablets contain a number or inert materials or additives, including those materials that help to impart satisfactory compression characteristics to the formulation, including diluents, binders, and lubricants. Other additives which help to give additional desirable physical characteristics to the finished tablet, such as disintegrators, coloring agents, flavoring agents, and sweetening agents might also be added in those compositions.

As used herein, "diluents" are inert substances added to increase the bulk of the formulation to make the tablet a practical size for compression. Commonly used diluents include calcium phosphate, calcium sulfate, lactose, kaolin, mannitol, sodium chloride, dry starch, powdered sugar, silica, and the like.

As used herein, "binders" are agents used to impart cohesive qualities to the powdered material. Binders, or "granulators" as they are sometimes known, impart cohesiveness to the tablet formulation, which insures the tablet remaining intact after compression, as well as improving the free-flowing qualities by the formulation of granules of desired hardness and size. Materials commonly used as binders include starch; gelatin; sugars, such as sucrose, glucose, dextrose, molasses, and lactose; natural and synthetic gums, such as acacia, sodium alginate, extract of Irish moss, panwar gum, ghatti gum, mucilage of isapol husks, carboxymethylcellulose, methylcellulose, polyvinylpyrrolidone, Veegum, microcrystalline cellulose, microcrystalline dextrose, amylose, and larch arabogalactan, and the like.

As used herein, "lubricants" are materials that perform a number of functions in tablet manufacture, such as improving the rate of flow of the tablet granulation, preventing adhesion of the tablet material to the surface of the dies and punches, reducing interparticle friction, and facilitating the ejection of the tablets from the die cavity. Commonly used lubricants include talc, magnesium stearate, calcium stearate, stearic acid, and hydrogenated vegetable oils.

As used herein, "disintegrators" or "disintegrants" are substances that facilitate the breakup or disintegration of tablets after administration. Materials serving as disintegrants have been chemically classified as starches, clays, celluloses, algins, or gums. Other disintegrators include Veegum HV, methylcellulose, agar, bentonite, cellulose and wood products, natural sponge, cation-exchange resins, alginic acid, guar gum, citrus pulp, cross-linked polyvinylpyrrolidone, carboxymethylcellulose, and the like.

As used herein, "coloring agents" are agents that give tablets a more pleasing appearance, and in addition help the manufacturer to control the product during its preparation and help the user to identify the product. Any of the approved certified water-soluble FD&C dyes, mixtures thereof, or their corresponding lakes may be used to color tablets. A color lake is the combination by adsorption of a water-soluble dye to a hydrous oxide of a heavy metal, resulting in an insoluble form of the dye.

As used herein, "flavoring agents" vary considerably in their chemical structure, ranging from simple esters, alcohols, and aldehydes to carbohydrates and complex volatile oils. Natural and synthetic flavors of almost any desired type are now available.

Further materials as well as formulation processing techniques and the like are set out in *The Science and Practice of Pharmacy* (Remington: The Science & Practice of Pharmacy), $22^{nd}$ Edition, 2012, Lloyd, Ed. Allen, Pharmaceutical Press, which is incorporated herein by reference.

The compositions of the invention can be in the forms of a powder or syrups.

As used here, "powders" means a solid dosage form intended to be suspended or dissolved in water or another liquid or mixed with soft foods prior to administration. Powders are typically prepared by spray drying or freeze drying of liquid formulations. Powders are advantageous due to flexibility, stability, rapid effect, and ease of administration.

According to a particular aspect, the compositions according to the present invention are useful for use in infant food formulations or in premixes (which are then used to produce infant food formulations). The premix is usually in a dry form. The premix is usually produced by mixing the composition according to the present invention with other suitable ingredients, which are useful and/or essential in an infant formulation and/or premix (or which are useful and/or essential for the production of an infant formulation and/or premix).

According to a particular aspect, an infant formulation in the context of the present invention is usually a dry formulation, which is then dissolved either in water or in milk.

The infant food premix or food formulations, may further contain auxiliary agents, for example antioxidants (such as ascorbic acid or salts thereof, tocopherols (synthetic or natural); butylated hydroxytoluene (BHT); butylated hydroxyanisole (BHA); propyl gallate; tert. butyl hydroxyquinoline and/or ascorbic acid esters of a fatty acid); ethoxyquin, plasticizers, stabilizers (such as soy lecithin, citric acid esters of mono- and di-glycerides, and the like), humectants (such as glycerine, sorbitol, polyethylene glycol), dyes, fragrances, fillers and buffers.

According to a further aspect of the present invention, is provided an infant formula as defined herein for use in promoting, assisting or achieving balanced growth or development in an infant or preventing or reducing the risk of unbalanced growth or development in an infant.

According to a particular aspect of the present invention, an infant formula may further comprise proteins fulfilling the minimum requirements for essential amino acid content and satisfactory growth, for example where over 50% by weight of the protein source is whey. Protein sources based on whey, casein and mixtures thereof may be used as well as protein sources based on soy. As far as whey proteins are concerned, the protein source may be based on acid whey or sweet whey (as readily available by-product of cheese making, preferably where caseino-glyco-macropeptide (CGMP) has been removed) or mixtures thereof and may include alpha-lactalbumin and beta-lactoglobulin in whatever desired proportions.

According to a particular aspect of the present invention, an infant formula may further comprise a carbohydrate source such as lactose, saccharose, maltodextrin, starch and mixtures thereof.

According to a particular aspect of the present invention, an infant formula may further comprise human milk oligosaccharides (HMOs).

According to a particular aspect of the present invention, an infant formula may further comprise a source of lipids including high oleic sunflower oil and high oleic safflower oil. The essential fatty acids linoleic and [alpha]-linolenic acid may also be added as may small amounts of oils containing high quantities of preformed arachidonic acid and docosahexaenoic acid such as fish oils or microbial oils. An infant formula may also contain all vitamins and minerals understood to be essential in the daily diet and in nutritionally significant amounts. Minimum requirements have been established for certain vitamins and minerals. Examples of minerals, vitamins and other nutrients optionally present in the infant formula include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chloride, potassium, sodium, selenium, chromium, molybdenum, taurine, and L-carnitine. An infant formula may optionally contain other substances which may have a beneficial effect such as fibres, lactoferrin, nucleotides, nucleosides, and the like.

According to a particular aspect, the compositions according to the present invention are useful for use in animal food formulations or premixes as feed additives.

According to a particular aspect, the animal food formulation according to the invention can be of any form, such as dry product, semi moist product, wet food product or a liquid and includes any food supplement, snack or treat. This includes, standard food products including liquids, as well as pet food snacks (for example, snack bars, pet chew, crunchy treat, cereal bars, snacks, biscuits and sweet products). Preferably, the pet foodstuff may be in the form of a dry foodstuff or wet foodstuff. The foodstuff of the first aspect of the invention is, in particular, a nutritionally balanced food product and/or food supplement, for example a pet product and/or pet supplement.

According to a particular embodiment, the animal food formulations or premixes may include one or more nutrients selected from essential amino acids (such as aspartic acid, serine, glutamic acid, glycine, alanine or proline) and essential lipids (such as myristic acid, palmitic acid, stearic acid, palmitoleic acid, oleic acid or linolenic acid).

The pet foodstuff may be any combination of nutrients from group (a) and group (b). The pet foodstuff may comprise aspartic acid, serine, glutamic acid, glycine, alanine or proline or any combination thereof and myristic acid, palmitic acid, stearic acid, palmitoleic acid, oleic acid or linolenic acid or any combination thereof.

In a further aspect of the invention, there is provided pet foodstuff comprising a glycan mixture of the invention.

In some embodiments, the compositions are useful as a pharmaceutical composition to treat a human suffering from obesity, diabetes, cardiometabolic diseases or low-grade inflammation.

In some embodiments, the compositions are useful as a pharmaceutical composition to be used in combination with an immunooncology treatment, e.g., treatment with an immune checkpoint inhibitor targeting the PD-1/PD-L1 axis.

According to one embodiment, the compositions stimulate or prime the immune system to recognize cancer cell surface glycans and thus treat the cancer.

Combinations

According to one embodiment of the invention, a composition according to the invention or a pharmaceutical formulation thereof is to be administered in combination with another active agent. In one aspect, the pharmaceutical composition of the invention may be administered in combination with an anti-cancer agent, such as at least one immunotherapeutic agent, in particular at least one immune check point inhibitor, such as a PD-1 inhibitor (for example anti-PD-1 antibody selected from nivolumab and pembrolizumab), PD-L1 inhibitor (for example anti-PDL-1 antibody selected from atezolizumab and durvalumab), or CTLA4 inhibitor (for example anti-CTLA4 antibody such as ipilimumab); an anti-CD52 (cluster of differentiation 52) antibody such as alemtuzumab; an anti-CD20 (B-lymphocyte antigen CD20) antibody selected from ofatumumab and rituximab; or at least one agent used in anti-cancer cytokine therapy, such as interferon and interleukin; or at least one agent used in CAR-T therapy, such as anti-CD19 CAR-T (B-lymphocyte antigen CD19-targeted chimeric antigen receptor T-cell therapy); or at least one agent used in dendritic cell therapy/oncolytic virus therapy.

In a more particular aspect, the mixture of glycans and glycopeptides according to this invention is to be used in combination with an immune checkpoint inhibitor targeting the PD-1/PD-L1 axis in the treatment of a cancer, particularly a cancer known to be responsive to such a checkpoint inhibitor.

According to another further aspect of the invention, is provided a mixture of glycans and glycopeptides according to the invention for use in the treatment of a cancer as a cancer vaccine or as a immune system primer for subsequent treatment with an antibody that is directed against a cancer cell surface glycan.

In an alternate aspect, a glycans and glycopeptides mixture or a composition of the invention may be administered in combination with an agent useful in the treatment of diabetes type 2 and obesity, such as liroglutide and exenatide.

The term "in combination with" includes the administration of a pharmaceutical composition of the invention to an individual prior to, or simultaneously with, or following administration of the other active therapeutic agent. For simultaneous administration, the pharmaceutical composition of the invention may, for example, additionally contain the other therapeutic agent (i.e., combined as a single dosage form). Alternatively, the pharmaceutical composition and the other therapeutic agent may be in separate dosage forms and be administered concomitantly. Such administration may be through the same or different formulation routes.

According to a particular aspect of the invention, a pharmaceutical composition of the invention is to be administered chronically (e.g. daily or weekly) for the duration of treatment and, optionally and additionally, prior to the administration of an anti-cancer agent.

According to another particular aspect of the invention, a pharmaceutical composition of the invention is to be administered in combination with an anti-cancer agent and additional therapeutic regimens or co-agents useful in the treatment of cancer (e.g. multiple drug regimens). These additional therapeutic regimens or co-agents are administered in a therapeutically effective amount, and include substances useful for treating, stabilizing, preventing, and/or delaying cancer such as substances used in conventional chemotherapy or radiotherapy directed against solid tumors and for control of establishment of metastases or any other molecule that act by triggering programmed cell death or with radio therapy.

According to another particular aspect of the invention, a glycans and glycopeptides mixture or a composition of the invention may be administered in combination with human milk oligosaccharides (HMOs).

Use of a Glycans and Glycopeptides Mixture According to the Invention

According to another particular aspect, the mixtures of the invention are useful for the preparation of nutritional supplement.

According to another particular aspect, the mixtures of the invention are useful for the preparation of nutritional supplement, in particular dietary or infant formulae.

According to another particular aspect, the mixtures of the invention are useful for the preparation pet food.

According to a particular aspect, the mixtures of the invention are useful to preserve the intestinal microbiota balance in adults or to favor the building of intestinal microbiota comparable with that found in breast fed babies in babies or infants which are not breast fed or not exclusively breast fed.

Also provided is the use of a mixture of the invention in the manufacture of a formula as defined herein. Also provided is a method for promoting, assisting or achieving balanced growth or development in an infant, wherein the method comprises administering to an infant a formula as defined herein.

According to another particular aspect, the mixtures of the invention are useful for the preparation of pharmaceutical formulations, in particular oral, rectal or topical formulations, more particularly oral formulations.

According to another particular aspect, the mixtures of the invention are useful for the prevention and/or treatment of an unbalance of the microbiota and/or disorders associated with dysbiosis such as asymptomatic dysbiotic microbiota, in particular depleted *Akkermansia muciniphila* gut's microbiota.

According to another particular aspect, the mixtures are to be fed to the subject at least once daily for at least a month.

Subjects

In an embodiment, subjects according to the invention are suffering from or at risk of suffering from depleted *Akkermansia muciniphila* gut's microbiota.

In another embodiment, subjects according to the invention are suffering from or at risk of suffering from a metabolic disorder such as obesity or metabolic syndrome.

In another embodiment, subjects according to the invention are suffering from or at risk of suffering from diabetes, in particular autoimmune diabetes.

In another embodiment, subjects according to the invention are suffering from a cancer, in particular subjects undergoing immunotherapy, radio therapy or chemotherapy. More particularly, subjects according to the invention are suffering from a cancer and are undergoing a treatment with immunotherapy such as checkpoint inhibitors, such as PD-1 immunotherapy (for example anti-PD-1 antibody selected from nivolumab and pembrolizumab), PD-L1 inhibitor (for example anti-PDL-1 antibody selected from atezolizumab and durvalumab), or CTLA4 inhibitor (for example anti-CTLA4 antibody selected from ipilimumab) or other anti-cancer agents, for example selected from an anti-CD52 (cluster of differentiation 52) antibody such as alemtuzumab; anti-CD20 (B-lymphocyte antigen CD20) antibody selected from ofatumumab and rituximab; an agent used in anti-cancer cytokine therapy such as interferon and interleukin; an agent in development for anti-cancer therapy such as in anti-CD19 CAR-T (B-lymphocyte antigen CD19-targeted chimeric antigen receptor T-cell therapy) cell therapy and dendritic cell therapy/oncolytic virus therapy.

In another embodiment, subjects according to the invention are babies or infants which not breast fed or not exclusively breast fed.

In another embodiment, subjects according to the invention are pets, in particular canine or feline pets.

Examples illustrating the invention will be described hereinafter in a more detailed manner and by reference to the embodiments represented in the Figures.

EXAMPLES

The following abbreviations refer respectively to the definitions below:
Am (*Akkermansia muciniphila* ATCC BAA835); Bl (*Bifidobacterium longum* subsp. *Infantis* ATCC 15697); Bt (*Bacteroides thetaiotaomicron* ATCC 29148); C1, C1, C1 (composition 1, 2 and 3); CC1, CC2, CC3 (comparative composition 1, 2 and 3); Fuc (fucose); Gal (galactose); GalNAc (N-Acetylgalactosamine); GalNH2 (galactosamine); Glc (glucose); GlcNAc (N-Acetylglucosamine); GlcNH2 (glucosamine); HPAEC-PAD (High-performance anion exchange chromatography with derivatization-free, pulsed amperometric detection); LC-MS/MS (liquid chromatography tandem-mass spectrometry); MM (minimal medium); NeuAc (N-Acetylneuraminic acid); NeuGc (N-glycolylneuraminic acid); OD (optical density).

Example 1: Production of Liquid and Solid Glycan Compositions According to the Invention A method of preparation of a glycan composition according to the invention was used to prepare two glycan compositions according to the invention:
- a mixture of glycans and glycopeptides as a liquid composition (C1) obtained by a method of the invention (Steps a-e);
- a mixture of glycans and glycopeptides as a solid composition (C2) obtained by a method of the invention (Steps a-h).

Two separate runs of the preparation were performed. In each run, the liquid composition (C1) is produced after step e, while the solid composition (C2) is produced by subjecting the liquid product of step e to concentration and drying steps f-h.

Step a:

10 g of mucin powder from porcine source (American laboratories, Inc.) as the isolated source of gastrointestinal tract mucins.

Step b: Release and Reduction of Glycans and Glycopeptides from Mucin

The mucin powder was put in a round-bottom flask (1 L) and a total of 100 ml of NaOH 0.1 M (0.4135 g in 100 ml; Sigma Aldrich, Cat #S5881-500 g) was added in three successive portions (3×33.3 ml) to facilitate the dissolution, at room temperature and under vigorous mixing with a PTFE (polytetrafluoroethylene) rod until a well homogenized mixture was obtained (of egg-like consistency). The high concentration of mucin lowered the pH of the solution to pH of less than 11±0.5. The flask was placed in an ice-bath and once the temperature of the reaction mixture was 5-10° C., 3.8217 g for run 1 or 3.8337 g for run 2 of 1 M $NaBH_4$ was added (Sigma Aldrich, Cat #213462-25 G or Cat #480886-25 G) under vigorous agitation and a white dense gelatinous/gummy matter, difficult to stir, was observed. After 5-8 minutes, the flask was put at room temperature and keep being mixed while the temperature increased to about 30° C. and slowly the gelatinous/gummy matter was converted in foam. A magnetic bar was added the flask to stir the solution and in the successive 40-60 minutes, the temperature was decreased to 20° C. and lot of foam formation was observed, an appropriate agitation was necessary to prevent foam getting out of the flask therefore hand-agitation was used every 5 minutes. After this time, the flask was put in a water bath and the reaction mixture was heated slowly in 1 hour to 48° C., always under stirring. The reaction mixture was kept at 48° C. under stirring for 20 hours in the flask that was not tightly closed to allow gas evacuation. The foam generation was monitored at least for the first 2-3 hours, and hand agitation was used when needed to prevent losing foam.

Step c: Neutralization

The flask was put in an ice bath and when the reaction temperature was 5-10° C., 0.5-1 ml portions of hydrochloric acid (HCl) (10M or ~5.2M) was added (Sigma Aldrich, Cat #320331-500 ML), under stirring, until pH was around 8, then the reaction flask was put at room temperature and neutralization was continued until the final pH=6.8-7 (7.4 ml of HCl 10M for run 1 or 11.7 ml of HCl ~5.2M for run 2 were required). Fume release was observed when pH was above 8. Foam was observed when pH was about 7-8 and stirring was vigorous. The weight and the volume of the neutralised reaction mixture was recorded (99 ml or 107, 1514 g of solution for run 1 and 87 ml or 126,9472 g of solution for run 2) and 10 ml of this solution were stored in fridge for future needs, therefore reducing the total volume of solution available for the next step.

Step d: First Filtration Step

The neutralized solution was filtered through Celite (diatomaceous earth) (Celite®S, 06858-1 Kg, Sigma-Aldrich) at room temperature. To 89 ml of reaction mixture for run 1, 6.4831 g of Celite® was added and to 77 ml of reaction mixture for run 2, 6.0614 g of Celite® was added and the mixtures were homogenized by mixing with a rod. This mixture was filtered on Buchner funnel with filter paper (Whatman 595, pore size 4-7 μm) with pressure (800-400 mbar) for about 30 minutes. The volume of filtrate obtained for run 1 was 64.5 ml (68.0832 g) and for run 2, 54 ml (57.7343 g). The Celite® cake formed on Buchner funnel was collected and re-suspended in an equal volume of water (for run 1, 89 ml or for run 2, 77 ml of deionized (D.I.) water) and filtered again as previously. The filtrate was collected (for run 1, 90 ml or 91.5271 g and for run 2, 79 ml or 80.0883 g). Both filtrates were unified/mixed to obtain for run 1, a total volume of 154.5 ml and for run 2, a total of 133 ml.

Step e: Second Filtration Step

The filtration was performed using SARTOFLOW Smart system equipped with 2 kD cassette (Sartocon Slice 200; Filter material: Hydrosart; Cut off: 2 kD; supplied by Sartorious Stedim), as follows:
(1) filtrates of reactions from run 1 and run 2 (154.5+ 133=287.5 ml) were unified and D.I. water was added to the final volume of 300 ml and loaded on Sartorius feed container;
(2) the magnetic agitation of the feed solution was set to 200-300 rpm;
(3) the following pressure settings were used: the PIRC2500=2.5 bar, PIR2600=1.5 bar, PIR2700=open;
(4) F-Perm (permeate flow) during the initial 3 hours was decreased slowly from 1.4 to about 0.5-0.8 g/min;
(5) the diafiltration mode was started once the initial feed weight was reduced to about 127.3 g and F-Perm was reduced to about 0.8-0.5 g/min;
(6) WIRC2100 value (setting the controller parameters and the alarm limits of the weight of the recirculation tank) was set to this 127.3 g weight value (the feed weight was kept constant at this set point value by adding D.I. water in the feed to compensate for the permeate leave), the F-Perm was increased slowly to 1.7-2 g/min after 5 hours of diafiltration and remained at this value for the successive 2 hours (until the end of the process);
(7) the diafiltration was considered completed when the weight of permeate is 6 times that of the WIRC2100 (6×127.3 g, about 763.8 g).

Step f: Collecting the Filtrate

The diafiltration was stopped and the retentate diafiltrate 2 kD was collected (also the sample contained in tubes); samples of permeate concentrate and permeate diafiltrate were stored. The liquid composition obtained was used as starting material for further steps g-h for preparing the solid composition.

Step g: Concentration 50 ml of retentate obtained from step e) above was placed in round-bottom flask and the concentration was performed using rotary evaporation until the volume was about 10 ml (reduction of the initial volume about 5 times). The concentration was performed at 50° C. (temperature of the evaporator) and the vacuum was regulated to the optimal value which ensures the highest rate of water removal (between 200 and 30 mbars), during concentration some sample (2-5 ml) might be lost.

Step h: Solvent Evaporation and Drying

The concentrated retentate obtained in step g) was split in two equal portions (5 ml each), one was kept for further analysis (composition C1) and the other was used to further make the solid composition (C2). To make C2, 20 ml of absolute ethanol (EtOH) was added to 5 ml of concentrated retentate, at room temperature, and a white precipitate was immediately observed. The sample was hand-agitated and then the solvent was evaporated in rotavapor, at 50° C., to dryness. The dried product was re-suspended in additional 20 ml of absolute EtOH followed by evaporation to dryness. The dried product had a very low solubility in EtOH, hence it was only partially dissolved. The addition of EtOH and successive solvent evaporation was repeated 2 more times (four total EtOH evaporations).

The flask containing the dried product was weighted and the net weight was calculated. From 5 ml of concentrated sample 1.1988 g of solid composition was obtained. If the total volume of final retentate diafiltrate 2 kD was used (133 ml) the expected dried product would be 6.38 g (31.9% of the starting material).

The conditions for the two runs are summarized in the Table 1B.

TABLE 1B

| Step | | Run 1 | Run 2 |
|---|---|---|---|
| a-b | Mucin (g) | 10.0292 | 10.0299 |
| | NaOH (g) | 0.4135 (0.8270/2) | 0.4135 (0.8270/2) |
| | NaBH$_4$ (g) | 3.8217 | 3.8337 |
| c | HCl (ml) | 7.4 (10 M) | 11.7 (~5.2 M) |
| | Reaction volume (ml) | 99 (of which 10 ml stored) | 87 (of which 10 ml stored) |
| d | Celite ® (g) | 6.4831 | 6.0614 |
| | First filtrate | 64.5 ml (68.0832 g) | 54 ml (57.7343 g) |
| | Celite ®-wash filtrate | 90 ml (91.5271 g) | 79 ml (80.0883 g) |
| | Unified filtrate (ml) | 154.5 | 133 |
| e-f | Feed for Filtration 2kDa | Unified filtrates (154.5 ml + 133 ml) + 12.5 ml (D.I. water) = 300 ml | |
| | Total Permeate of 2 kDa diafiltration 2 kDa (g) | 763.8 g (Sartorius weight value, approx. 1 g = 1 ml) | |
| | Final Retentate Diafiltrate (ml) (liquid composition 1) | 133 ml (135.5319 g) | |
| a-f | Total water used (ml) | 100 + 100 + 89 + 77 + 12.5 + 763.8 = 1142.3 | |
| g | concentration | | |
| h | Total EtOH (ml) | 4 × 20 = 80 | |
| | Final dried product (solid composition 2) | 6.38 g* *only 25 ml of liquid composition were evaporated with 4 × EtOH and dried | |

A final solid composition (C3) was prepared by combining four different runs that were carried through step h and used for all further analysis and testing.

Production of Comparative Glycan Compositions

Three separate preparations of a comparative composition containing mostly free glycans (e.g., with a glycopeptide: glycan ratio of less than 1:2) (CC1, CC2 and CC3) were prepared as follows:

O-glycans were released from porcine gastric mucin (Sigma Type III, 10% w/v) by incubation at 48° C. for 20 hrs in 150 mM NaOH with 750 mM NaBH$_4$ and the pH of that solution was maintained at more than 11.5 to 12.5 by adding more NaOH if necessary. The reaction was neutralized with HCl (10 M). Insoluble material was removed by centrifugation at 1,4000×g (30 min, 4° C.). Supernatant was filtered and dialyzed against distilled H$_2$O with 1 kD MWCO (molecular weight cut-off) membranes (Spectra/Por 7, Spectrum Labs) and subsequently lyophilized. Glycans were solubilized in 50 mM Tris pH 7.4 buffer and fractionated using DEAE-Sepharose CL-6B anion exchange columns.

Example 2: Characterization of Compositions According to the Invention

The liquid and solid compositions (C1, C2) obtained by the process set forth of the invention as described in Example 1 have been characterized for their elemental, oligosaccharide and monosaccharide contents.

Elemental analysis was performed by various standardized methods and results are presented in Table 2.

TABLE 2

| Elements | C1 | C2 |
|---|---|---|
| C (%) | <0.3 | 43.1 |
| H(%) | 13.3 | 7.1 |
| N (%) | 0.6 | 8.2 |
| B (mg/Kg) | <1 | 200 |
| Cl total (mg/Kg) | 7 | 700 |
| F (mg/Kg) | <500 | <500 |
| Na (mg/Kg) | 400 | 10000 |
| P (mg/Kg) | 300 | 7000 |
| S total (mg/Kg) | 300 | 6000 |
| As (mg/Kg) | <1 | <1 |
| Cd (mg/Kg) | <1 | <1 |
| Pb (mg/Kg) | <1 | <1 |
| Hg (mg/Kg) | <1 | <1 |

The results show that boron (B) content in both the C1 and C2 of the invention was equal or less than 200 parts per million (ppm). This shows the removal of NaBH$_4$ a potentially toxic contaminants in these compositions.

Glycan Analysis

Figures 1C, 1D:
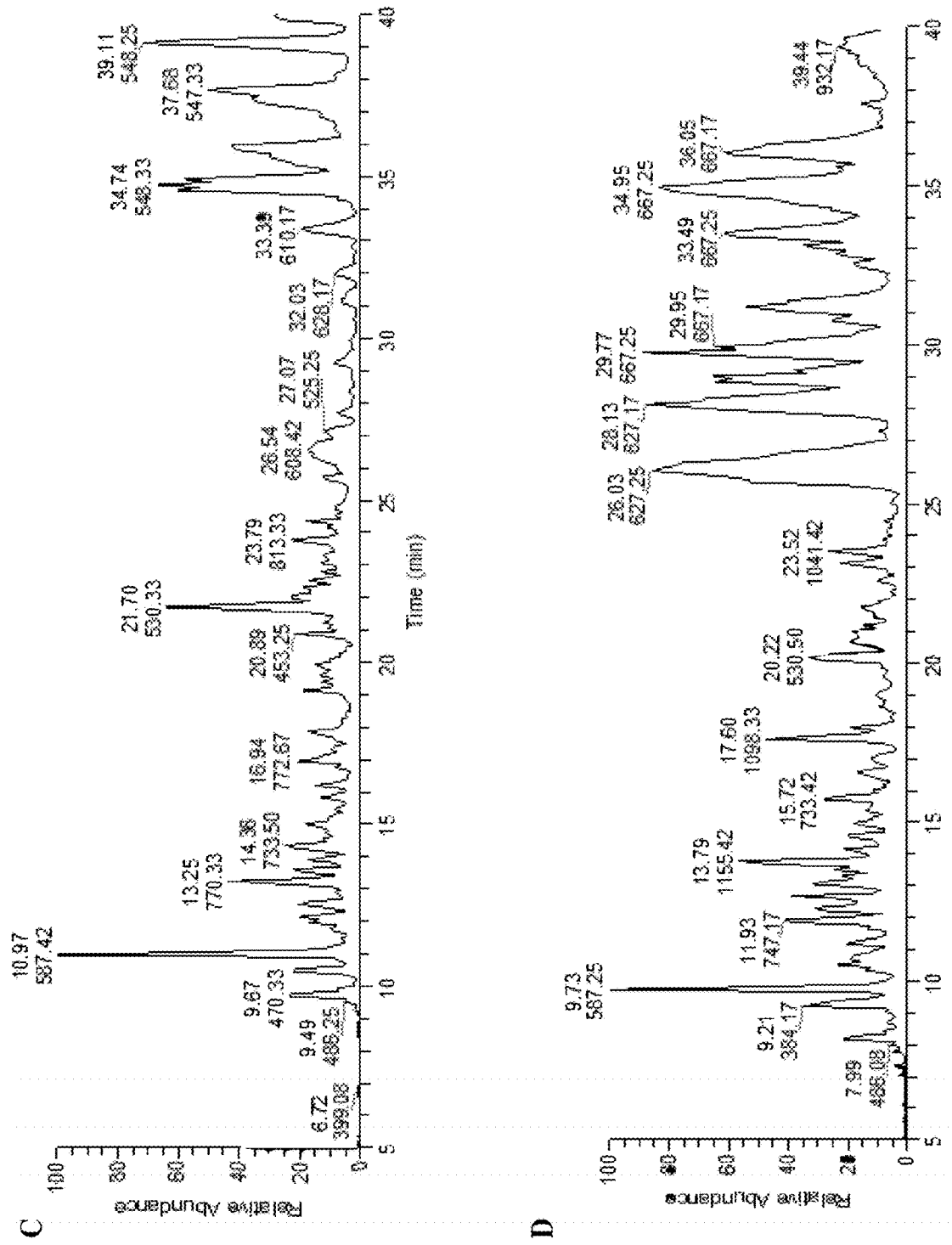
Figure 1E:
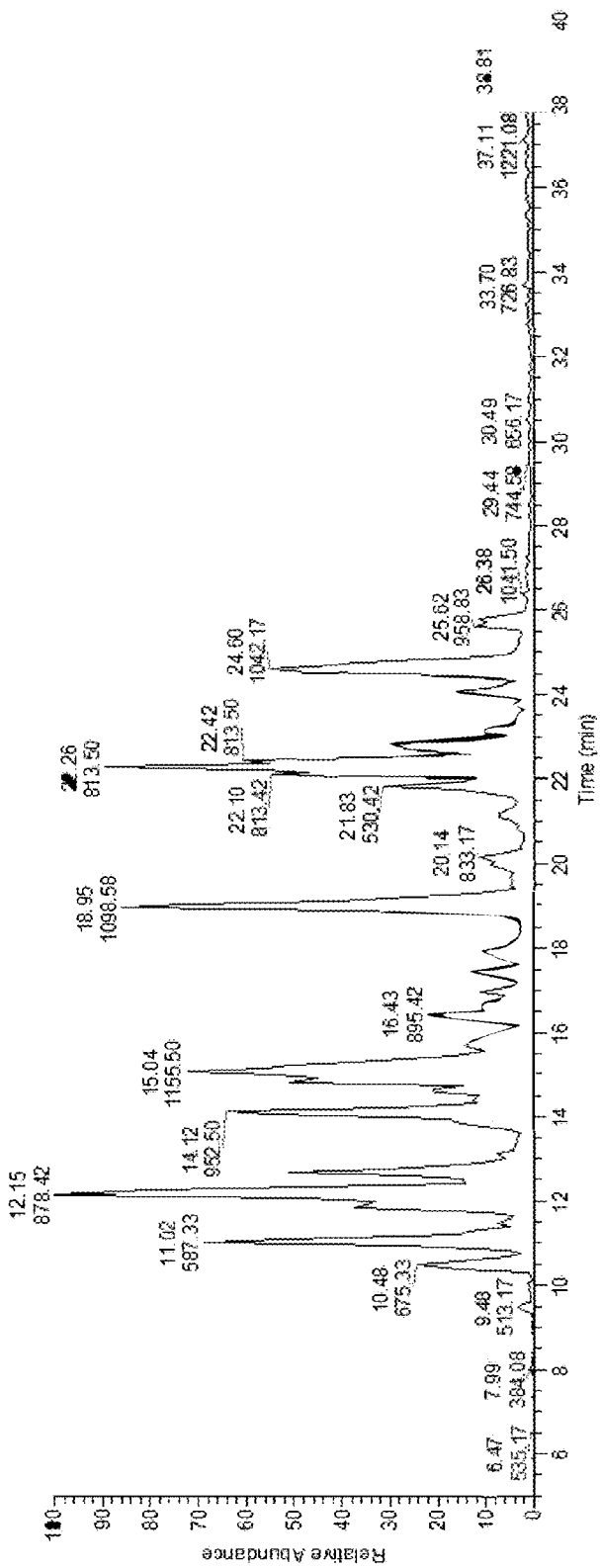

Sample Preparation and Analysis:

samples of both C1 (5 ml) and C2 (9 mg) preparations were filtered via a 30-kDa spin filter. The filtrated samples were tested for glycan content with orcinol-sulphuric acid and by LC-MS/MS according to formula (i) as described above. After 80% acetone precipitation of C1, 17.9 mg material was recovered from supernatant. This material from C2 contained at least 13% glycan by LC-MS/MS, which was consistent with orcinol-sulphuric acid result (26%). The glycans contained reduced O-glycans (68%) and peeling product/degraded glycans (32%). In C2, 35% of total glycan were detected in the fraction obtained with a filter size between 2 and 30 kDa. The remaining fraction over 30 kDa was believed to contain glycans which were still attached to (glyco)peptides and/or (glyco)proteins. To remove most glycoproteins and glycopeptides, the samples were precipitated with cold 80% acetone. The supernatant was dried (17.9 mg obtained from C1 and 6.9 mg from C2) and reconstituted to 10 mg/ml. The samples were analyzed by LC-MS/MS (liquid chromatography tandem-mass spectrometry) at a concentration of 1 mg/ml (FIG. 1). Most O-glycans were eluted between 5 and 22 min, while non-glycan compounds were eluted after 22 min. The spectra of C1 were sufficient for further analysis. A further purification of C2 was performed before further analysis. Samples (100 µl) of each composition (C1 and C2) were passed through C18 cartridge and reconstituted with 100 µl. The samples were analyzed by LC-MS/MS under the same conditions as previously (FIGS. 1C & 1D). The signals of both samples were improved but still mixed with non-glycan products. Both spectra were used for structural characterization. Analysis of a sample of comparative glycan composition CC1 (10 mg/ml) was analyzed directly from LC spectra (FIG. 1E). Next, the glycan content and composition analysis was performed on both C1 and C2 compositions by HPAEC-PAD (high-performance anion exchange chromatography with derivatization-free, pulsed amperometric detection) after acid hydrolysis of product to corresponding monosaccharides.

Liquid Composition C1:

44 oligosaccharides were detected and it contained both O-glycans (n=28) and their peeling products (n=16) and some oligosaccharides were found with non-reducing end (n=10). After 80% acetone precipitation, 17.9 mg material was recovered from supernatant. This material contained at least 13% glycan (w/w), which was consistent with orcinol-sulphuric acid result (26%). The glycans contained reduced O-glycans (68%) and peeling product/degraded glycans (32%).

Solid Composition C2:

46 oligosaccharides were detected and it contained both O-glycans (n=31) and their peeling products (n=15) and some oligosaccharides were found with non-reducing end (n=7). After 80% acetone precipitation, 6.9 mg material was recovered from 9 mg powder. This material contained at least 12% (w/w) glycan, which was lower than that from orcinol-sulphuric acid result (35%). The glycans contained reduced O-glycans (53%) and peeling product/degraded glycans (47%).

Comparative Composition CC1:

109 oligosaccharides were detected and contained both 0-glycans (n=100) and their peeling products (n=9). This material contained at least 65% glycan (w/w).

Table 3 reports two separate analyses of the amounts of each monosaccharide (Fuc—Fucose; Gal—galactose; $GalNH_2$—galactosamine; Glc—glucose; $GlcNH_2$—glucosamine) in the solid composition prepared by steps a) through h) in Example 1 and their sum giving the total glycan content, as analyzed by HPAEC-PAD.

TABLE 3

| Monosaccharide content in mg/L for 100 mg/L loaded | | | | | | |
|---|---|---|---|---|---|---|
| Sample | Fuc | $GalNH_2$ | $GlcNH_2$ | Gal | Glc | Total |
| Analysis 1 | 3.629 | 7.672 | 15.223 | 9.570 | 1.909 | 38.003 |
| Analysis 2 | 3.883 | 6.448 | 14.123 | 8.668 | 1.479 | 34.601 |

Figure 2A:
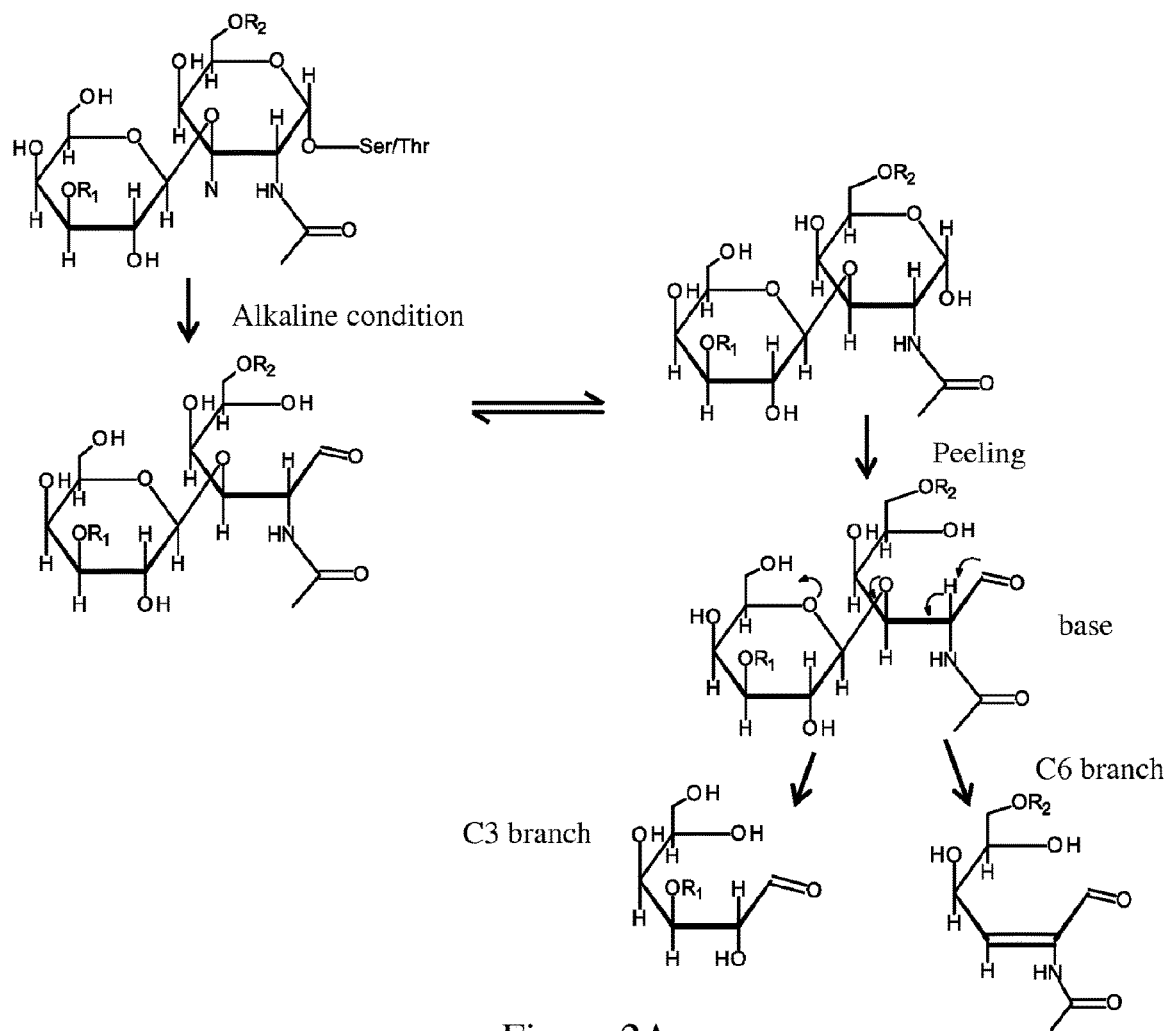
FIG. 2 shows a schematic representation of peeling reactions occurring during reductive β-elimination (A) and of the conversion of the core 2 glycans (B) and the formation of core glycans C3 branch and C6 branch after cut of bond β-3, as described in Example 2.
Figure 2B:
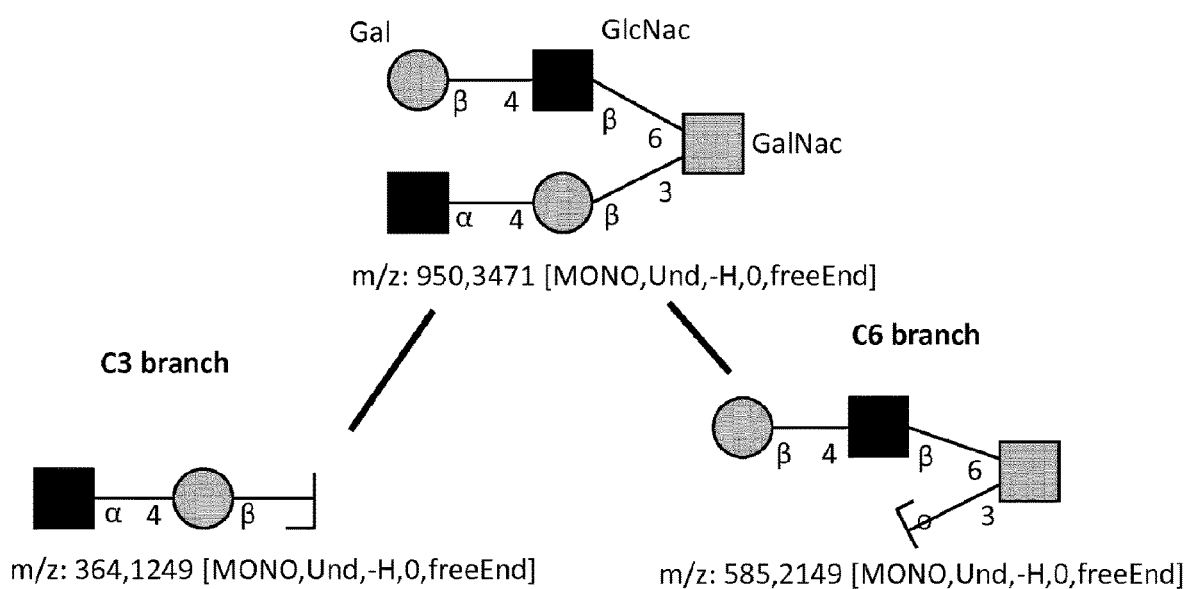

For both C1 and C2 compositions of Example 1, the peeling reaction was caused by relative more alkaline and less $NaBH_4$ during reductive β-elimination (step b). Core 1 glycan (Galβ1→3GalNAc) as major constituent of O-glycans are generally converted to core 2 oligosaccharides (Galβ1→3(GlcNAcβ1→6) GalNAc). In case of core 2 O-glycans, the peeling reaction resulted in two types of degraded products, one containing C6 branch of N-acetyl-galactosamine (GalNAc) and another containing C3 branch of GalNAc (as schematized in FIGS. 2A and B). In case of extended core 1 O-glycans, the peeling reaction would remove terminal residue from non-reducing end one by one. If the aldehyde is not reduced by $NaBH_4$, it results in a mixture of aldehyde and alditol in the sample. Table 4 shows the physical and chemical properties of the pooled solid compositions (C3).

TABLE 4

| Purity | 33 to 36% of glycan |
|---|---|
| Glycan Structure Diversity | 46 |
| Appearance | White brown dried powder. |
| Solubility | Water soluble |
| | (80 to 120 g/L at 25° C.) |
| Chemical/Physical proprieties: | |
| Carbohydrate | 33 to 36% |
| Proteins | 51% |
| Boron (ppm) | 200 |
| Moisture | 2-5% |
| pH | 8.2 (2% w/v, in |
| | DI water at 20° C.) |
| Microbiological: | |
| Salmonella | Negative |
| E. coli | Negative |
| Total plate count | Less than 10'000 CFU/g |

Therefore, those data support that compositions obtained by a method of the invention allowing releasing glycans and glycopeptides from the mucin source resulted in compositions comprising a mixture of glycans and glycopeptides with

- higher glycopeptide:glycan ratio compared to CC1. The ratio in the combined solid C3 preparation is between 51:33 and 51:36. CC1 has less than 10% protein/glycopeptide suggesting a glycopeptide:free glycan ratio of about 1:10.
- less diverse free glycan content (28 different free glycan species in C1 of Example 1, 31 different free glycan species in the solid composition of Example 1 and 40 different free glycan species in the combined solid composition C3 than found in CC1 (100 different free glycan species).

Example 3: Effects of a Composition of the Invention on Bacteria Growth

The pooled solid compositions (C3) and comparative glycan compositions (CC2, CC3) obtained as described in Example 1 have been assessed for their ability to provide carbon source for the growth of three anaerobic bacteria that resides in the human intestinal tract i.e.: *Bifidobacterium longum* subsp. *Infantis* ATCC 15697 (Bl; gram-positive), *Bacteroides thetaiotaomicron* ATCC 29148 (Bt; gram-negative), and *Akkermansia muciniphila* ATCC BAA835 (Am; gram-negative), as compared to Glucose (Glc) as follows:

The various carbon sources (C3, CC2, CC3 and glucose (Glc)) were resuspended at 20% (w/v) in water and sterilized by filtration. Since C3, CC2, CC3 were viscous, a part of the compositions may have remained in the filter. A minimal medium (MM) for colony growth was prepared according to Marcobal et al., 2011, *Cell Host & Microbe*, 10, 507-514. Compositions C3, CC2 and CC3 were added to the MM to obtain a final concentration of 1.5% (w./v.) of glycans, Glc was added to the MM to obtain a final concentration of 0.5%, and MM alone was used as a further control.

200 µl-cultures were performed in 96-well plates under anaerobic atmosphere produced by the GENBAG ANAER system (Biomérieux, 45534). Volumes of inoculum of the bacteria were adapted to obtain a starting optical density (OD) at 600 nm of approximately 0.1 (about $10^7$ cells) and OD was further measured at the start of the experiment and after 24, 48 and 72 h of bacterial growth. Growth experiments were done in triplicate with three independent cultures of Bl, Bt and Am and an additional experiment with one culture of Am was performed.

Figure 3:
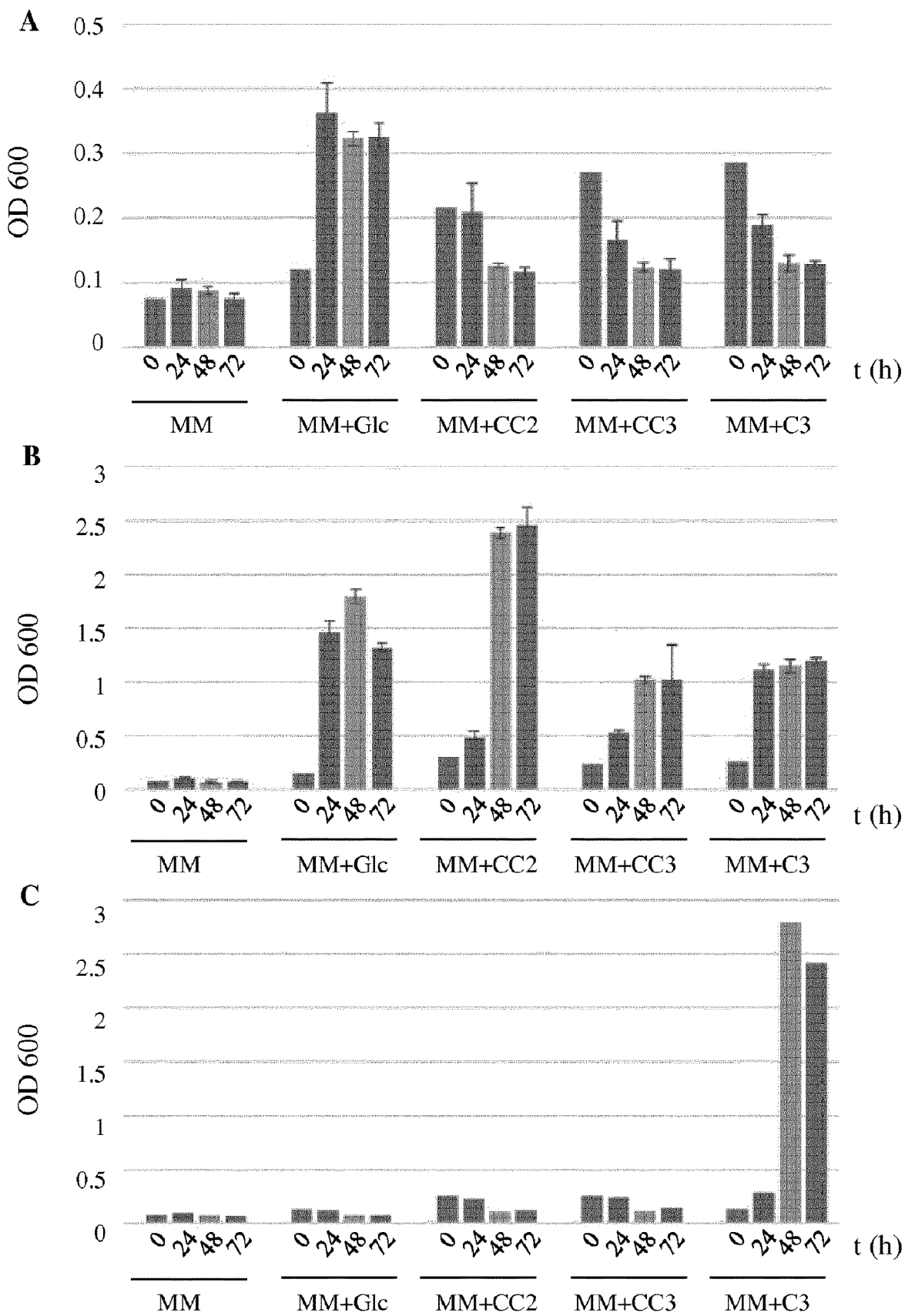
FIG. 3 shows bacterial concentrations (as measured by optical density (OD) at 600 nm) versus incubation time (t) for different commensal gut bacteria strains grown ex vivo in minimal medium alone (MM), in the presence of a glycan composition of the invention (C3), in glycan compositions prepared by different methodologies and outside the scope of the present invention (CC2, CC3), or in glucose alone (Glc), as described in Example 3. A: Bl; B: Bt and C, D: Am (C: 3 Am cultures; D: 1 Am culture).
Figure 3:
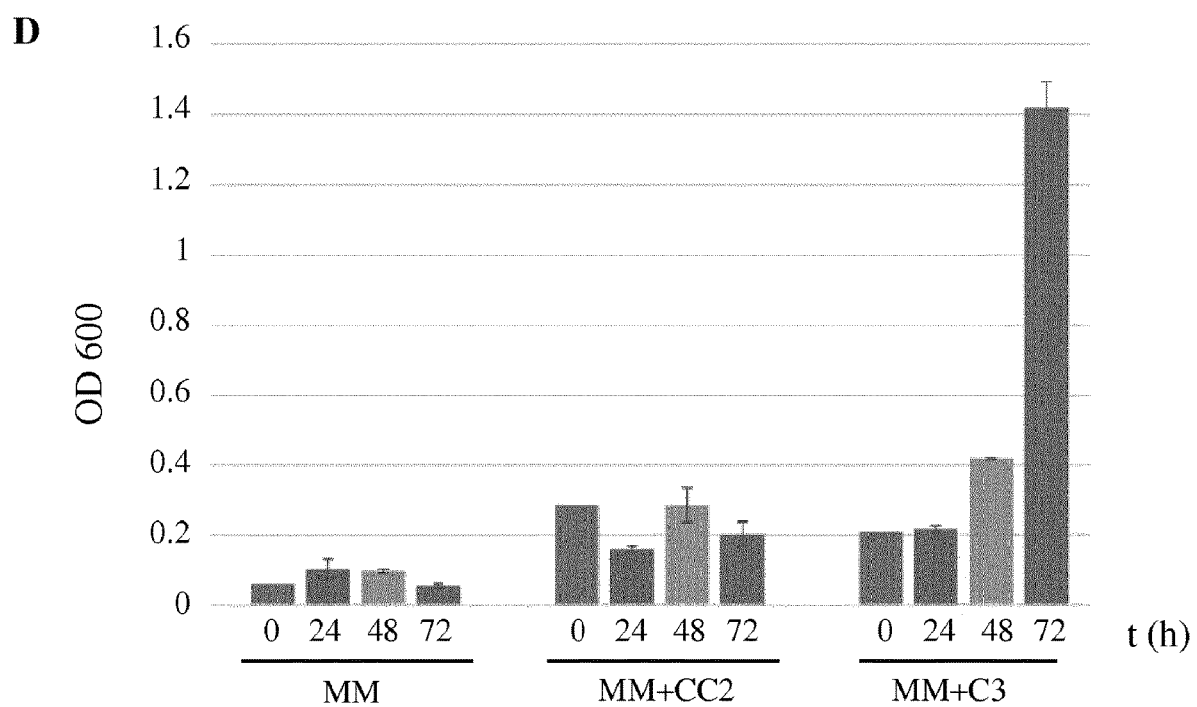

Only cultures supplemented with Glc caused an increase in $OD_{600}$ of the Bl strain beyond that at the 0 time point (FIG. 3A). All tested carbon sources (C3, CC2, CC3, Glc) caused an increase in $OD_{600}$ of the Bt strain above that at the 0 time point (FIG. 3B). Only C3 caused an increase in $OD_{600}$ of the Am strain above that at the 0 time point (FIGS. 3C and D).

These data support that, although purified Microbiota Accessible Carbohydrates (MACs) obtained by known methods (comparative compositions CC2 and CC3) were able to cause growth of *Bacteroides thetaiotaomicron* (Bt) similar to what is observed in the presence of glucose, none could provide for *Akkermansia muciniphila* growth. Advantageously, a glycan composition according to the invention has proven to be able to serve as a carbon source for *Akkermansia muciniphila* growth, which suggest that such compositions will be useful for treating a gut dysbiosis, in particular in infants and patients with depleted *Akkermansia muciniphila* population.

The invention claimed is:

1. A composition comprising 3 or more different glycans and a ratio of glycopeptides: free glycans (w/w) between 51:33 and 51:36, wherein the glycopeptides were obtained from the hydrolysis of gastrointestinal tract mucins; and the composition is capable of promoting the growth of *Akkermansia muciniphila* in a mammalian gut.

2. The composition of claim 1, wherein the composition is a powder or syrup.

3. The composition of claim 1, wherein the composition comprises 85%-90% protein and carbohydrate.

4. The composition according to claim 1, wherein the gastrointestinal tract mucins are porcine gastrointestinal tract mucins.

5. An infant food premix or infant food formulation comprising the composition according to claim 1.

6. An animal feed comprising the composition according to claim 1.

7. The animal feed according to claim 6, wherein the animal feed comprises an essential amino acid or essential lipid.

8. A pharmaceutical composition comprising the composition according to claim 1 and a pharmaceutically acceptable carrier, diluent or excipient thereof.

9. The composition of claim 1, wherein the hydrolysis of gastrointestinal tract mucins is achieved under conditions maintaining a pH below 11.5.

10. The composition of claim 9, wherein the hydrolysis of gastrointestinal tract mucins is achieved under conditions maintaining the pH between 10.5 and less than 11.5.

11. The composition of claim 1, wherein the composition comprises between 70-90% (w/w) glycopeptide.

12. A method of treating an unbalance of the microbiota and/or dysbiosis in a subject in need thereof, comprising administering to the subject the composition of claim 1.

13. The method according to claim 12, wherein the subject is a human.

14. The method according to claim 13, wherein the human is an infant.

15. The method according to claim 13, wherein the human has a disorder selected from obesity, metabolic syndrome, diabetes, asymptomatic dysbiotic microbiota, and immune dysfunction.

16. The method according to claim 12, wherein the subject is a domesticated animal.

17. A method of increasing the prevalence of *Akkermansia muciniphila* in a mammalian subject's gut, comprising administering to the mammalian subject the composition of claim 1.

18. The method according to claim 17, wherein the composition is obtained from gastrointestinal tract mucins.

19. The method according to claim 17, wherein the subject is a human or domesticated animal.

\* \* \* \* \*